(12) United States Patent
Wright

(10) Patent No.: US 8,993,289 B1
(45) Date of Patent: Mar. 31, 2015

(54) HIGH-PERFORMANCE BIOCOMPOSITES, BIOPOLYMERS, BIOEXPLOSIVES, AND BIOADHESIVES MADE FROM BIOMESITYLENE

(71) Applicant: The United States of America as Represented by the Secretary of the Navy, Washington, DC (US)

(72) Inventor: Michael E. Wright, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/770,094

(22) Filed: Feb. 19, 2013

Related U.S. Application Data

(60) Provisional application No. 61/599,682, filed on Feb. 16, 2012.

(51) Int. Cl.
| | |
|---|---|
| *C07C 51/285* | (2006.01) |
| *C12P 5/00* | (2006.01) |
| *B01J 23/20* | (2006.01) |
| *C07C 231/14* | (2006.01) |
| *C07C 63/24* | (2006.01) |
| *C07C 63/307* | (2006.01) |

(52) U.S. Cl.
CPC .............. *C12P 5/005* (2013.01); *B01J 23/20* (2013.01); *C07C 231/14* (2013.01); *C07C 51/285* (2013.01); *C07C 63/24* (2013.01); *C07C 63/307* (2013.01)
USPC ........................................................ 435/166

(58) Field of Classification Search
None
See application file for complete search history.

(56) References Cited

U.S. PATENT DOCUMENTS

| | | | |
|---|---|---|---|
| 2,917,561 A | 12/1959 | Eby et al. | |
| 5,030,749 A * | 7/1991 | Hussmann | ................... 562/414 |
| 5,087,781 A | 2/1992 | Schutz et al. | |
| 2012/0059205 A1 * | 3/2012 | Rusek | .......................... 585/302 |

OTHER PUBLICATIONS

Ezeji et al. "Production of acetone, butanol, and ethanol by Clostridium beijerinckii BA101 and in situ recovery by gas stripping" (2003) World Journal of Microbiology & Biotechnology: vol. 19: 595-603.*
Ezeji et al. "Butanol Production from Agricultural Residues: Impact of Degradation Products on Clostridium beijerinckii Growth and Butanol Fermentation" (Aug. 2007) Biotechnology & Bioengineering, vol. 97, No. 6: 1460-1469.*
Polyamide pseudorotaxanes, rotaxanes, and catananes based on Bis (5-carboxyl-1,3-phenylene)-(3x+2)-crown-x ethers, Macr. 2004, 37, 7514-7529.
Peroxidative oxidation of benzene and mesitylene by vanadium catalysts, J. of Mol. Cata. A: Chem 224 (2004) 189-195.
Cyclic & linear polyamides form polycondensations of hexamethylenediame & m-xylylenediamine wiht adipic, isophthalic, and terephthalic acids, Macromole. 2009, 42, 2336-2343.
U.S. Appl. No. 13/942,798, Michael Wright.

* cited by examiner

*Primary Examiner* — Jon P Weber
*Assistant Examiner* — Teresa E Knight
(74) *Attorney, Agent, or Firm* — Charlene A. Haley

(57) ABSTRACT

A biomass is used to prepare bio-acetone which is converted to bio-mesitylene in high chemical yield and selectivity and the latter is converted using continuous flow chemical processes to a variety of functionalized bioaromatics that are useful in the preparation of high performance biopolymers, biocomposites, bio-explosives, and bio-adhesives.

4 Claims, 3 Drawing Sheets

HIGH-PERFORMANCE BIOCOMPOSITES, BIOPOLYMERS, BIOEXPLOSIVES, AND BIOADHESIVES MADE FROM BIOMESITYLENE

CROSS-REFERENCE TO RELATED APPLICATIONS

This is a non-provisional patent application, claiming the benefit of, parent application Ser. No. 61/599,682 filed on Feb. 16, 2012, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to methods for converting biomass to bio-mesitylene. The latter is then converted to intermediates useful in making high performance polymers, bio-explosives, bio-composites, and/or bio-adhesives.

Figure 1:
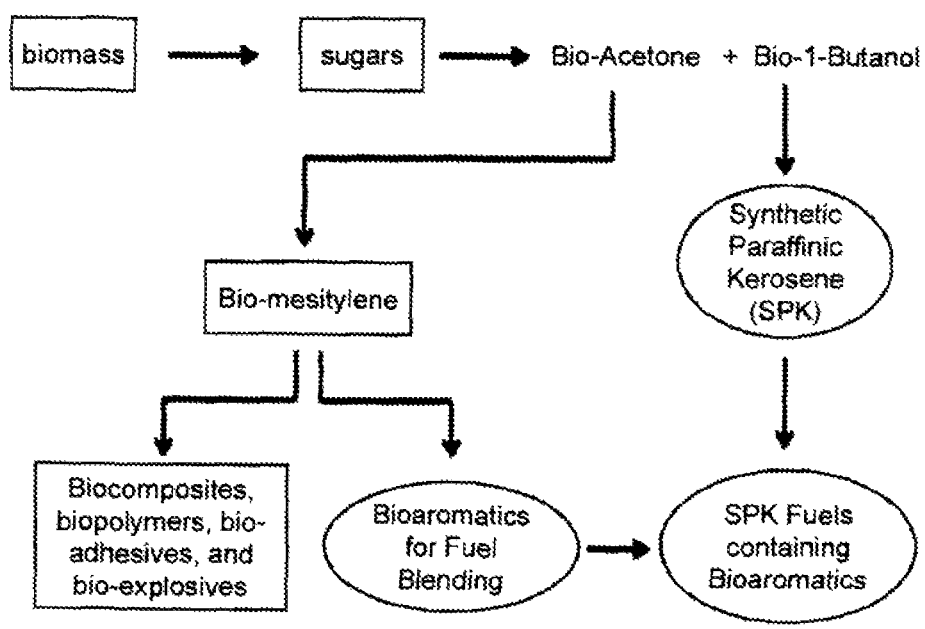
FIG. 1 is general process flow diagram showing how biomass is processed to release sugars that are then used to prepare a mixture of bio-acetone and bio-1-butanol. The bio-acetone is used to prepare bio-mesitylene which is used to prepare two useful categories of new bio-mesitylene derived products, according to embodiments of the invention.
Figure 2:
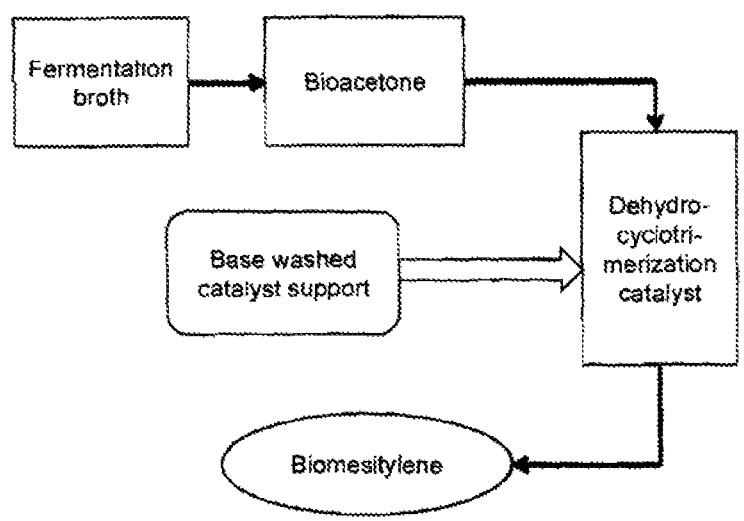
FIG. 2 is a diagram showing a general process flow diagram for the conversion of biomass sugars to bio-mesitylene using a dehydrocyclotrimerization catalyst prepared from base washed catalyst support, according to embodiments of the invention.
Figure 3:
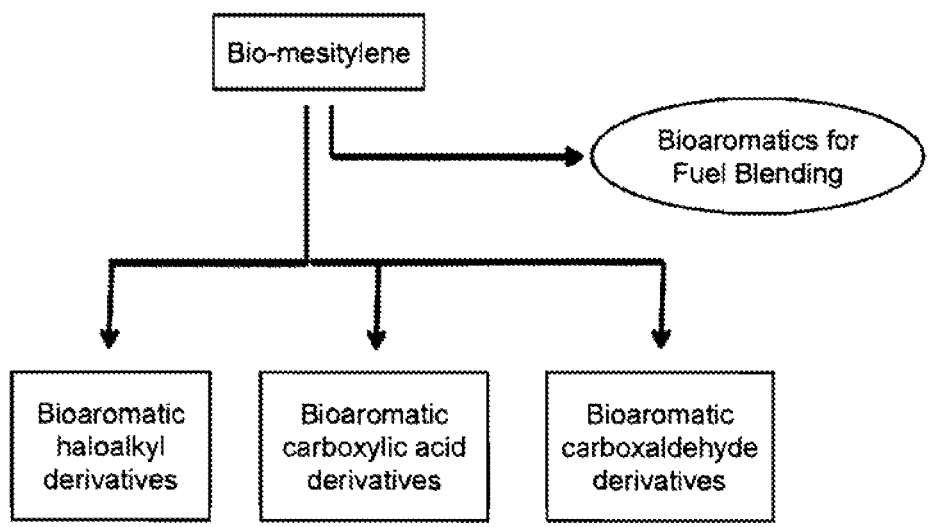
FIG. 3 shows the general flow scheme showing the conversion of biomesitylene to three categories of bioaromatics, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to a method of starting with biomass and creating bio-acetone through a process of first sugar extraction that includes the cellulosic and/or the hemi-cellulosic sugars followed by fermentation using at least one bio-organism, typically a strain of bacteria or yeast (Schematic 1).

Biomass conversion to 1-biobutanol is rapidly advancing to the commercialization from non-food sources and in these new acetone-butanol-ethanol (ABE) processes, ethanol production is nearly taken to zero and the acetone production is limited to ~25 wt-% of the n-butanol production. Even with this current selectivity for bio-n-butanol, significant amounts of bio-acetone are available from waste biomass. Although it is well known that acetone can be converted to mesitylene, the catalysts and processes lack chemical conversion efficiencies and time on stream. Embodiments of these inventions address these shortcomings. Thus, bio-mesitylene can be made readily from biomass according to the embodiments of this invention. Prior to this invention there is no route for taking non-food biomass and converting this to well defined high performance aromatic polymers, biocomposites, bio-explosives, and/or bio-adhesives. The current embodiments of the invention teach how biomass can be used to prepare all these crucial materials that possess exceptional physical and chemical properties and are prepared using chemistry that is fully sustainable and made from fully renewable chemical resources. Importantly, the biomass sources used in embodiments of this invention do not compete with food production.

There are numerous reports on the chemistry of mesitylene as prepared from petroleum resources as well as trimesic acid (also known as 1,3,5-benzenetricarboxylic acid). Some recent work on isophthalic acid to prepare high-performance polyamides are of particular interest [N. Singletary et al. Macromolecules 2009, 42(7), pp 2336-2343]:

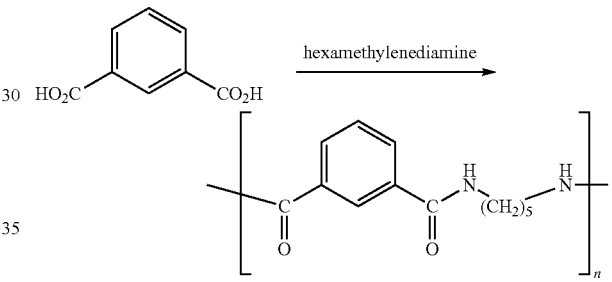

In embodiments of the invention, the starting monomer is prepared from petroleum sources and does not provide a sustainable source of high performance polymers and/or adhesives.

Work from Virginia Tech has demonstrated the versatility of isophthalic acid-core in preparing many interesting polymer systems [H. W. Gibson et al. Macromolecules 2004, 37(20), pp 7514-7529]. The extension to 5-methyl isophthalic (uvitic acid) is a useful and interesting extension of previous work in the area. The work by Gibson et al. relied on petroleum sources for all chemicals is thus not a sustainable technology. In contrast, embodiments of this invention teach a highly efficient and unexpected route to high performance aromatic polymers from readily available and cost effective nonfood biomass or waste cellulosic materials.

Chemistries are known for oxidizing the methyl groups on aromatic rings to corresponding carboxylic acid groups. Some work has examined selective oxidation [e.g. see: P. M. Rais et al. J. Mol. Catalysis A: Chem. 2004, 224(1-2), pp 189-195], namely one methyl group at a time. However, yields and selectively are low in these papers and the work does not teach a process nor chemistry that can be used to prepare useful bioaromatics for then preparing high performance bioaromatic polymers, aromatic bio-explosives, nor bioaromatic adhesives.

The fermentation process leads to a mixture of organic compounds dominated by n-butanol, acetone, and ethanol in a ratio determined by the specific bio-organism used. This product ratio can be tailored by natural selection techniques for the bio-cultures to optimize for acetone and/or n-butanol production.

The n-butanol product can be dehydrated to form bio-1-butene with high selectivity and chemical yield in prior patent applications by applicant has been found to be useful in preparing oligomeric materials that can be converted into high flashpoint (>61° C.) synthetic paraffinic kerosene (SPK) fuels for use in turbine and diesel engines.

Other useful co-products including carbon dioxide and hydrogen are produced in the fermentation process and can be used for creating biofuels and biolubricants in prior patent applications by applicant. In general terms the mesitylene produced from the bio-acetone can be used to create high performance biopolymers, biocomposites, bio-adhesives, and bio-expolosives that are a direct result of embodiments of this invention. Other uses for the mesitylene can be to form alkylated bio-mesitylenes which can be used as blending component for SPK fuels. These alkylated-bio-mesitylenes provide a wide range of boiling points (about 120° C. to about 300° C.). A wide range of boiling points is known to those experienced in the art of fuel blending to have distinct advantages. The process more fully described in prior patent applications by applicant allows for the first time a rapid and efficient conversion of biomass to bioaromatics which are ideally suited for blending with SPK based fuels that can be used directly in turbine and diesel engines and have physical and chemical properties that meet or exceed the requirements of ASTM D1655 and ASTM 7566 (turbine) and ASTM 1975 (diesel). Blending provides the ability to finely tune the physical properties of the final SPK-bioaromatic fuel to consistent levels that cannot be achieved by processes producing bio-aromatics concurrently with the SPK fuel generation process from biomass feedstocks.

The acetone is isolated by a distillation process that resembles a stripping process and passed directly into heated column containing a supported catalyst-system. Previous work in the field [Eby et al. in U.S. Pat. No. 2,917,561; 1959] has shown that tantalum oxides supported on silica or alumina can convert acetone to mesitylene in 62% conversion with 100% selectivity. Although it is suggested that the unreacted acetone can be recycled, this costs energy in the process making it less efficient and less sustainable/renewable. The embodiments of the invention provide a catalyst system and chemical process to afford mesitylene with 98-100% selectivity and greater than 98% chemical conversion of acetone to the target biomesitylene (Schematic 2). The catalyst used in the heated reactor is a silica or alumina oxide treated with base, washed with water, and then air dried for 24 h at about 100° C. to about 150° C. The solid support should have a surface area of 10 to 500 m²/g with another embodiment of about 100 m²/g. The treated support is then exposed to a solution of at least one Group 5 transition metal complex at levels ranging from 0.1 to 10 wt-% (metal complex wt to that of total support wt). The solution is removed and the catalyst air dried and then further heated for 24 h at about 150 to 400° C. in air.

In some cases it can be advantageous to treat the Group 5 supported catalyst with a hydrocarbon solution of at least one organosilane or siloxane reagent that is capable of reaction with the surface. This creates a hydrophobic-catalytic surface which can provide enhanced catalyst performance and time on stream in certain cases. In general, arylsilanes and arylsiloxanes are embodiments due to their thermal stability relative to alkylsilanes and alkyl-siloxanes.

The acetone entering the can include varying amounts of water since obtaining dry acetone is energy intensive and not needed for the catalysts prepared in embodiments of this invention. Thus, the acetone can include between 0.0001 wt-% and 40 wt-% water and present no negative effects on conversion and chemical selectivity for biomesitylene, this has not previously been noted or demonstrated in studies and patents regarding petroleum based acetone conversion to mesitylene [Schutz et al. U.S. Pat. No. 5,087,781; 1991].

The acetone is heated to about 200° C. to about 400° C. prior to making contact with the dehydrocyclotrimerization catalyst which is maintained at a temperature between about 250° C. and about 400° C., with between about 350° C. and about 375° C. temperature in other embodiments. Contact time for the acetone vapors with the supported catalyst varies with water content with an embodiment having a range of 0.1 to 500 seconds with another embodiment of about 1 to 10 seconds.

The biomesitylene prepared as the instant result of embodiment of this invention is now converted to three general categories of modified mesitylenes, each can serve as monomers and/or precursors to monomers that are useful for the manufacturing high performance biopolymers, biocomposites, bio-adhesives, and bio-explosives (Schematic 3). Although some art in the field has been described using mesitylene to prepare monomers [JP 7,807,795; JP 7,868,760; JP 7,397,830], the fact it is difficult to isolate from petroleum sources has limited its use in preparing high performance polymers and other derivatives.

Chemistries are known for oxidizing aromatic methyl groups to corresponding carboxylic acids and it can be performed in a somewhat selective manner [e.g. see: P. M. Reis et al. J. Mol. Catalysis A: Chem. 2004, 224(1-2), pp 189-195]:

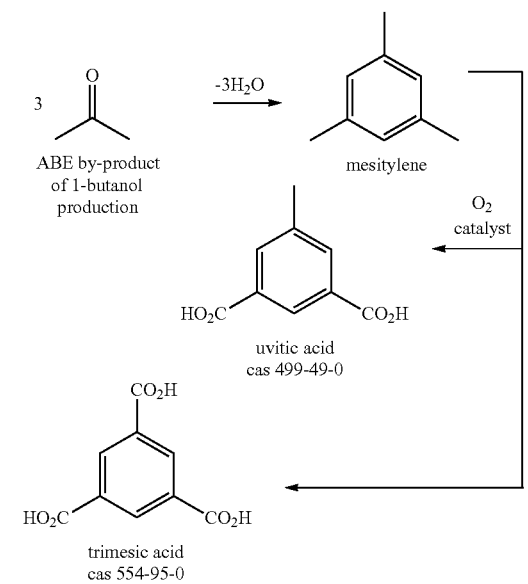

Trimesic and uvitic acids prepared in this invention are trinitrated to create bioexplosives:

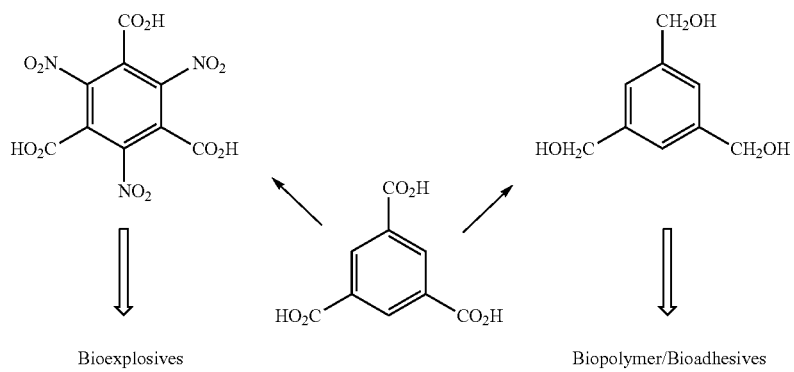 [SMILES: O=C(O)c1c([N+](=O)[O-])c(C(=O)O)c([N+](=O)[O-])c(C(=O)O)c1[N+](=O)[O-] ; O=C(O)c1cc(C(=O)O)cc(C(=O)O)c1 ; OCc1cc(CO)cc(CO)c1]

Bioexplosives

Biopolymer/Bioadhesives

The carboxylic acids groups of the trinitrated trimesic acid are converted to amides with by reaction with amines including from zero to three additional nitrogen atoms. Several methods are available for conversion of the carboxylic acid group to the respective amides. Typically this is done by simple heating of the acid in the presence of at least one amine and the water by-product is removed by distillation. Other methods for converting carboxylic acids to amides using coupling agents, for example dicyclohexylcarbodiimide (DCC), can be used in the case of bio-trimesic acid reactions as well. A third alternative is to convert the bio-trimesic acid to the respective trimesic acid chloride by treatment with thionyl chloride or phosphorus trichloride followed by simple treatment with the amine in the presence of an acid scavenger (e.g. triethyl amine). Conversion of the bio-trinitrated trimesic acid to respective bio-trinitrato triamido benzene can be accomplished by other methods known to those in the art. Examples of amines that are of particular value in embodiment of the invention are heterocyclic amines such 2-aminoimidazole and other five- and six-membered rings including additional nitrogen atoms over and beyond the nitrogen used to create the amide bond. The optimum nitrogen to oxygen ratio based on wt-% for these new bio-explosives is similar to that of triamino trinitrobenzene (TATB), an explosive known to those familiar with the art of energetic materials.

The bio-trinitrated triamido benzene is best purified by recrystallization from at least one solvent. A combination of non-polar and polar organic solvents affords the best combination to produce uniform crystal size of the bio-explosive. Non polar organic solvents include, but not limited to, aliphatic and aromatic hydrocarbons and ethers. Polar organic solvents include, but not limited to, aliphatic and aromatic esters and amides, Removal of the non-polar solvent from the mixture by fractionation can be used to induce crystallization of the bioexplosive.

The bio-mesitylene prepared as a result of embodiments of this invention are selectively oxidized to uvitic acid by use of cobalt catalysts at levels of 0.05 to 5 wt-% loading, activation of the catalyst can be achieved by using a peroxide or similar compound. The oxidant of choice is oxygen delivered as a gas. The uvitic acid is separated from co-oxidant products and used in polymeriation chemistry or nitration chemistry to prepare high performance polymers or bioexplosives, respectively.

More extensive exposure of the bio-trimetylene to the oxidation conditions affords the bio-trimesic acid. Other, more traditional chemical oxidants including potassium permanganate can be used to convert bio-mesitylene to bio-trimesic acid since selective oxidation is not required.

An example of polymers that can be prepared from uvitic acid prepared from biomass:

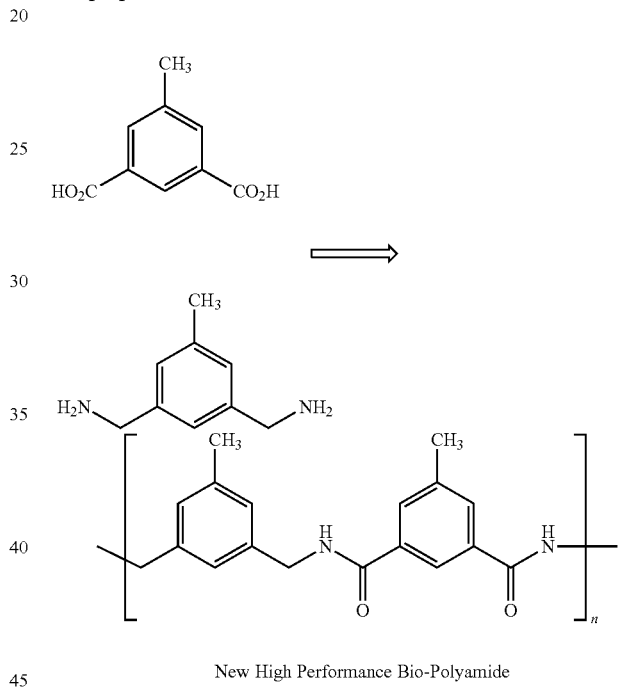

New High Performance Bio-Polyamide

Other aromatic diamines, for example 1,3-diaminobenzene, can be placed in contact with uvitic acid and heated to cause formation of the amide linkages, thus creating Nomex® like polyamides, well known for their exceptional mechanical and flame resistance. Aliphatic diamines and be used, including 1,6-diaminohexane, can be used to prepare polyamides more closely related to polyamides generally classified as "nylons."

Uvitic acid can be reduced using metal catalysts in the presence of hydrogen or by chemical reduction with alane- or borane-hydride reagents well known to those experienced with carboxylic acid reductions to the corresponding 5-methyl-1,3-bis(hydroxymethyl)benzene. The latter compound can be converted to reactive epoxides by reaction with epichloro hydrin and similar reagents. The 5-methyl-1,3-bis(hydroxymethyl)benzene is readily converted to respective 5-methyl-1,3-bis(chloromethyl)benzene that is converted to 5-methyl-1,3-bis(aminomethyl)benzene by treatment with ammonia. These reactive epoxides can be used in the formation of bio-epoxy resins and as bio-adhesives:

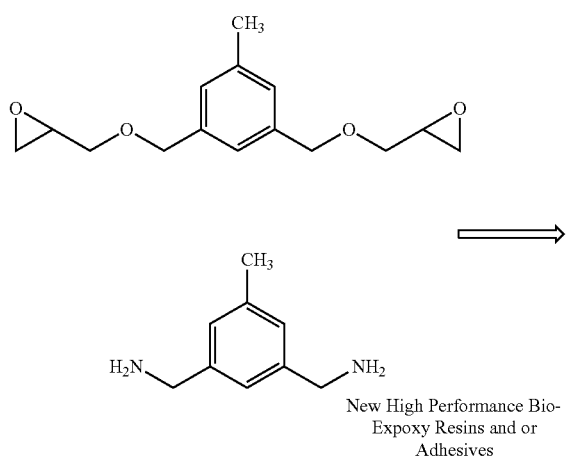

New High Performance Bio-
Expoxy Resins and or
Adhesives

The bio-expoxy resins prepared in this embodiment can be cured in the presence of carbon and/or glass fibers to create bio-composites which have similar mechanical and physical properties to epoxy composites prepared from petroleum.

An aspect of the invention generally relates to methods for preparing bio-mesitylene from biomass including treating a biomass with an aqueous solution or extraction media and an acid catalyst to produce a mixture of hemi-cellulosic and cellulosic sugars, fermenting the mixture of sugars utilizing at least one bio-organism to a fermentation broth having n-butanol, acetone, and ethanol, stripping the acetone from the fermentation broth by sparging with a gas and condensed to forming a liquid substantially having acetone, contacting the acetone with a heated and solid supported dehydration-cyclotrimerization catalyst for a period of 1 to about 500 seconds at pressures ranging from about 0 psig to about 1000 psig, and collecting the bio-mesitylene and purifying the bio-mesitylene by fractionation.

Embodiments of the invention include the biomass being selected from the group consisting of grasses, plants, trees, and waste biomass. In embodiments, the bio-organism is at least one strain of bacteria and or yeast. In embodiments, the sparging gas is selected from the group consisting of at least one gas taken from nitrogen, argon, carbon dioxide, or C1 to C4 saturated hydrocarbon. In embodiments, the supported catalyst is prepared from based treated aluminum oxide support and having from 0.0 to 5 wt-% of a Group metal oxide dispersed over the aluminum oxide support. Another aspect of the invention generally relates to bioaromatics haloalkyl derivatives, bioaromatic carboxylic acid derivatives, and/or bioaromatic carboxaldehyde derivatives produced by the methods herein.

Another aspect of the invention generally relates to methods for preparing a dehydration-cyclotrimerization catalyst including, first treating of gamma-alumina with an aqueous base solution for a period of about 5 minutes to about 120 minutes forming a solid, removing the aqueous solution by filtration or decanting and washing the solid with water, second treating of the gamma-alumina with an aqueous solution of a Group 5 metal and removing the water by evaporation to produce a modified gamma-alumina having from 0 to 5 wt-% of a Group 5 metal complex, and heating the modified alumina at about 200° C.-about 500° C. in air for a period of about 4 hours to 24 hours, and forming the dried and modified alumina dehydration-cyclotrimerization catalyst into a powder or pellets.

Another aspect of the invention generally relates to methods of preparing bio-uvitic acid including, subjecting mesitylene to oxidation chemistry utilizing a cobalt catalyst with $O_2$ gas and peroxide to form bio-uvitic acid. Yet another aspect of the invention generally relates to methods of preparing bio-trimesic acid including subjecting mesitylene to oxidation chemistry utilizing a cobalt catalyst with $O_2$ gas and peroxide to form bio-trimesic acid.

Embodiments of the invention further include preparing biopolyamides by mixing the bio-uvitic acid with bio-1,3-di (aminomethyl)-5-methylbenzene to produce biopolyamide. Embodiments of the invention further include preparing bio-explosives from bio-trimesic by mixing the bio-trimesic acid with at least one nitrating agent to produce a first mixture of bio-trinitrated trimesic acid, adding at least one non-solvent to the first mixture to precipitate the bio-trinitrated trimesic acid, drying the precipitate bio-trinitrated trimesic acid under reduced pressure for about 1 torr to about 24 hours at 30° C. to about 100° C., contacting the dry bio-trinitrated trimesic acid with at least one amine and at least one solvent producing a second mixture that is heated from about 50° C. to about 150° C. for period of about 2 hours to about 48 hours, adding at least one non-solvent to the second mixture to precipitate the bio-trinitrated triamido benzene, isolating the bio-trinitrated triamido benzene by filtration, and drying the bio-trinitrated triamido benzene under at a reduced pressure of about 1 torr to about 700 torr at a temperature of about 20° C. to about 100° C. Embodiments further include mixing the trimesic acid with polymerization chemistry to produce biopolymers and/or bioadhesives.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for preparing bio-mesitylene from biomass, comprising:
treating a biomass with an aqueous solution or extraction media and an acid catalyst to produce a mixture of hemi-cellulosic and cellulosic sugars;
fermenting said mixture of sugars utilizing at least one bio-organism to a fermentation broth having n-butanol, acetone, and ethanol;
stripping said acetone from said fermentation broth by sparging with a gas and condensed to forming a liquid substantially having acetone;
contacting said acetone with a heat treated solid supported dehydration-cyclotrimerization catalyst treated with arylsilanes, arylsiloxanes, alkylsilanes, and/or alkylsiloxanes for a period of 1 to about 500 seconds at pressures ranging from about 0.02 psig (1 torr to about 1000 psig, wherein said supported catalyst is prepared from based treated aluminum and/or silicon oxide support and having from 0.1 to 5 wt-% of a Group 5 metal oxide dispersed over said aluminum and/or silicon oxide support; and collecting said bio-mesitylene and purifying said bio-mesitylene by fractionation.

2. The methods according to claim 1, wherein said biomass is selected from the group consisting of grasses, plants, trees, and waste biomass.

3. The methods according to claim 1, wherein said bio-organism is at least one strain of bacteria and/or yeast.

4. The methods according to claim 1, wherein said sparging gas is selected from the group consisting of at least one gas taken from nitrogen, argon, carbon dioxide, or C1 to C4 saturated hydrocarbon.

\* \* \* \* \*